US012633398B2

(12) United States Patent
Sargent et al.

(10) Patent No.: US 12,633,398 B2
(45) Date of Patent: May 19, 2026

(54) ARTIFICIAL INTELLIGENCE FOR ALLEVIATING CHERRY-PICKING IN RADIOLOGY

(71) Applicant: International Business Machines Corporation, Armonk, NY (US)

(72) Inventors: Dustin Michael Sargent, San Diego, CA (US); Christina Carr, Rescue, CA (US); Sun Young Park, San Diego, CA (US); David Gruen, Weston, CT (US)

(73) Assignee: International Business Machines Corporation, Armonk, NY (US)

( * ) Notice: Subject to any disclaimer, the term of this patent is extended or adjusted under 35 U.S.C. 154(b) by 1096 days.

(21) Appl. No.: 17/652,297

(22) Filed: Feb. 24, 2022

(65) Prior Publication Data

US 2023/0268060 A1      Aug. 24, 2023

(51) Int. Cl.
| | |
|---|---|
| *G16H 40/20* | (2018.01) |
| *G06N 3/045* | (2023.01) |
| *G06N 3/08* | (2023.01) |
| *G16H 15/00* | (2018.01) |
| *G16H 30/20* | (2018.01) |

(52) U.S. Cl.
CPC ............. *G16H 40/20* (2018.01); *G06N 3/045* (2023.01); *G06N 3/08* (2013.01); *G16H 15/00* (2018.01); *G16H 30/20* (2018.01)

(58) Field of Classification Search
CPC ........ G16H 40/20; G16H 10/60; G16H 30/40; G16H 50/20; G16H 50/70; G06Q 10/1097
USPC ........................................................ 705/2–3
See application file for complete search history.

(56) References Cited

U.S. PATENT DOCUMENTS

| | | | | |
|---|---|---|---|---|
| 10,045,218 | B1 * | 8/2018 | Stapleton | ................. G06N 5/01 |
| 10,909,646 | B2 * | 2/2021 | Esposito | ........... G06Q 10/0631 |
| 11,663,039 | B2 * | 5/2023 | Tzortzatos | ............. G06N 3/006 |
| | | | | 706/12 |
| 2011/0218815 | A1 | 9/2011 | Reiner | |
| 2015/0149193 | A1 | 5/2015 | Jester | |
| 2017/0358047 | A1 | 12/2017 | Esposito | |
| 2020/0265946 | A1 * | 8/2020 | Benjamin | .............. G16H 30/20 |

(Continued)

FOREIGN PATENT DOCUMENTS

WO      WO-2021180551 A1 *  9/2021   ............. G16H 30/40

OTHER PUBLICATIONS

Isaacson, Jenelle, "Orchestrating Radiology Workflow in a Large, Distributed Reading Environment." Published Jun. 25, 2021 by Imagine Technology News, 4 pages, https://www.itnonline.com/content/blogs/jenelle-isaacson-contributing-editor/blog-orchestrating-radiology-workflow-large (Year: 2021).*

(Continued)

*Primary Examiner* — Joy Chng
(74) *Attorney, Agent, or Firm* — Seed Intellectual Property Law Group LLP

(57)      ABSTRACT

A system may receive radiology data, outcome data for one or more exams, and elapsed time data for the one or more exams. The system may train a first machine learning algorithm to detect exams that are candidates for cherry-picking using the set of radiology data, outcome, and elapsed time data. The system may further determine, using the radiology data and the first machine learning algorithm, a likelihood that an exam was rejected due to cherry-picking.

17 Claims, 4 Drawing Sheets

(56) References Cited

U.S. PATENT DOCUMENTS

2023/0049758 A1 * 2/2023 Park ....................... G16H 30/20

OTHER PUBLICATIONS

Holzberger, Karen, "Hunting for the 'easy' button: Finding balance and minimizing radiology overhead." Published Nov. 19, 2018 by Nuance, 6 pages, https://whatsnext.nuance.com/healthcare/hunting-for-the-easy-button-finding-balance-and-minimizing-radiology-overhead/ (Year: 2018).*

Esposito, Michael. "Imaging Informatics: Filling the Gaps in Imaging Workflow," Accessed Oct. 9, 2021. 3 pages. In Radiology Today, vol. 21 No. 2 p. 8. Published by Radiology Today. https://www.radiologytoday.net/archive/rt0220p8.shtml.

Holzberger, Karen. "Hunting for the 'easy' button: Finding balance and minimizing radiology overhead." Published Nov. 19, 2018 by Nuance. 6 pages. https://whatsnext.nuance.com/healthcare/hunting-for-the-easy-button-finding-balance-and-minimizing-radiology-overhead/.

Isaacson, Jenelle. "Orchestrating Radiology Workflow in a Large, Distributed Reading Environment." Published Jun. 25, 2021 by Imagine Technology News. 4 pages. https://www.itnonline.com/content/blogs/jenelle-isaacson-contributing-editor/blog-orchestrating-radiology-workflow-large.

Mell, et al., "The NIST Definition of Cloud Computing," Recommendations of the National Institute of Standards and Technology, U.S. Department of Commerce, Special Publication 800-145, Sep. 2011, 7 pgs.

Weiss, David. "Cherry picking: Slowly I turned . . . " Published Jul. 7, 2008 by Applied Radiology. 2 pages. https://www.appliedradiology.com/articles/guest-editorialcherry-picking-slowly-i-turned.

* cited by examiner

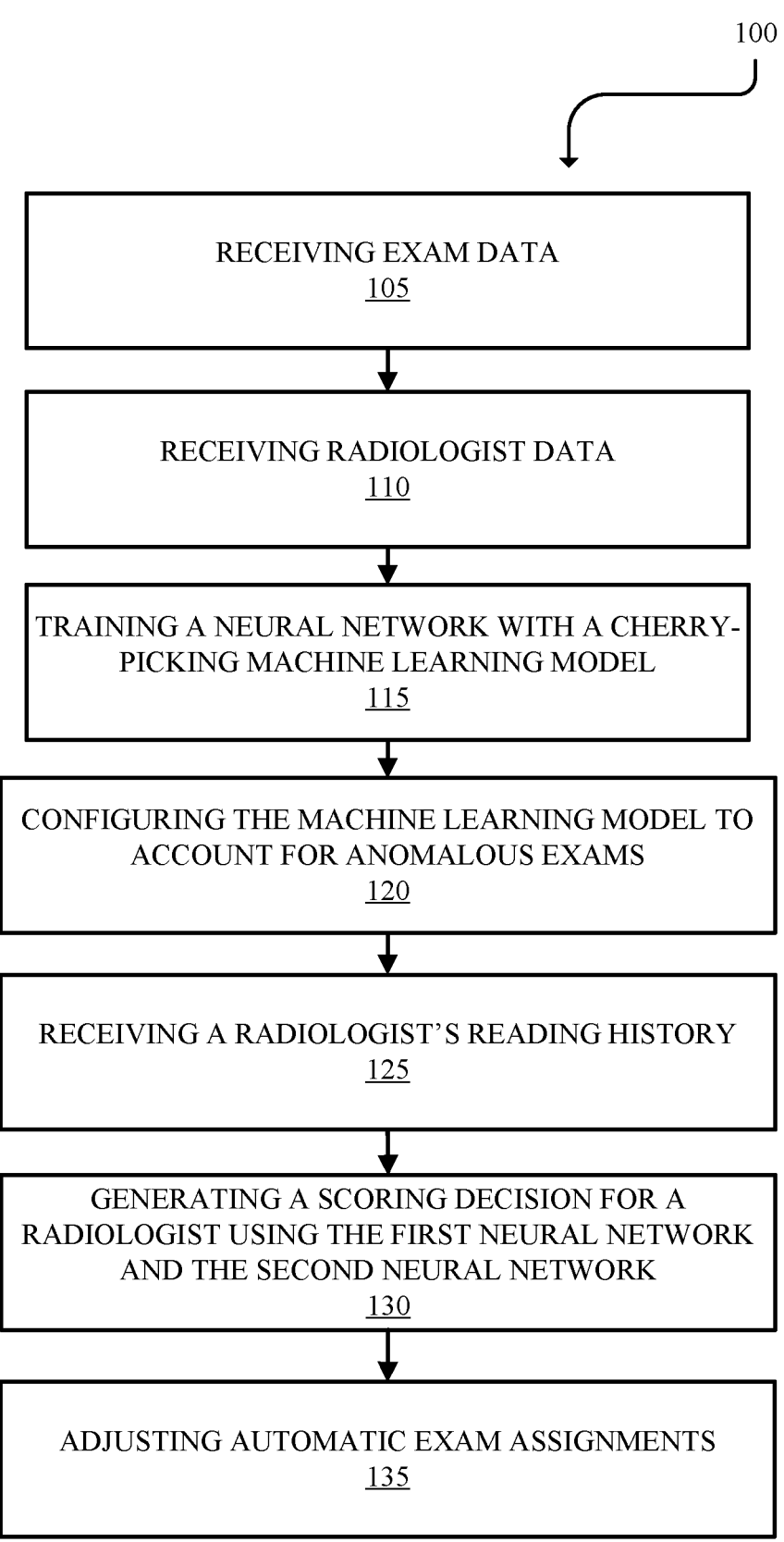

100

RECEIVING EXAM DATA
105

RECEIVING RADIOLOGIST DATA
110

TRAINING A NEURAL NETWORK WITH A CHERRY-
PICKING MACHINE LEARNING MODEL
115

CONFIGURING THE MACHINE LEARNING MODEL TO
ACCOUNT FOR ANOMALOUS EXAMS
120

RECEIVING A RADIOLOGIST'S READING HISTORY
125

GENERATING A SCORING DECISION FOR A
RADIOLOGIST USING THE FIRST NEURAL NETWORK
AND THE SECOND NEURAL NETWORK
130

ADJUSTING AUTOMATIC EXAM ASSIGNMENTS
135

FIG. 1

ARTIFICIAL INTELLIGENCE FOR ALLEVIATING CHERRY-PICKING IN RADIOLOGY

BACKGROUND

Aspects of the present disclosure relate to artificial intelligence systems for alleviating cherry-picking in radiology.

Image viewing software, such as picture archiving and communication system (PACS), are used in healthcare organizations to securely store and digitally transmit electronic images and clinically-relevant reports. Radiologists use PACS to select and read exams. Such software allows geographically dispersed groups to use teleradiology to complete their examinations around the globe.

BRIEF SUMMARY

The present disclosure provides a method, computer program product, and system of alleviating cherry-picking in radiology with artificial intelligence (AI). In some embodiments, the method includes receiving radiology data, outcome data for one or more exams, and elapsed time data for the one or more exams, training a first machine learning algorithm to detect exams that are candidates for cherry-picking using the set of radiology data, outcome, and elapsed time data, and determining, using the radiology data and the first machine learning algorithm, a likelihood that an exam was rejected due to cherry-picking.

Some embodiments of the present disclosure can also be illustrated by a computer program product comprising a computer readable storage medium having program instructions embodied therewith, the program instructions executable by a processor to cause the processors to perform a method, the method comprising receiving radiology data, outcome data for one or more exams, and elapsed time data for the one or more exams, training a first machine learning algorithm to detect exams that are candidates for cherry-picking using the set of radiology data, outcome, and elapsed time data, and determining, using the radiology data and the first machine learning algorithm, a likelihood that an exam was rejected due to cherry-picking.

Some embodiments of the present disclosure can also be illustrated by a system comprising a processor and a memory in communication with the processor, the memory containing program instructions that, when executed by the processor, are configured to cause the processor to perform a method, the method comprising receiving radiology data, outcome data for one or more exams, and elapsed time data for the one or more exams, training a first machine learning algorithm to detect exams that are candidates for cherry-picking using the set of radiology data, outcome, and elapsed time data, and determining, using the radiology data and the first machine learning algorithm, a likelihood that an exam was rejected due to cherry-picking.

BRIEF DESCRIPTION OF THE DRAWINGS

FIG. 1 illustrates an example method of alleviating cherry-picking in radiology with artificial intelligence (AI), according to various embodiments of the present invention.

DETAILED DESCRIPTION

Figure 2:
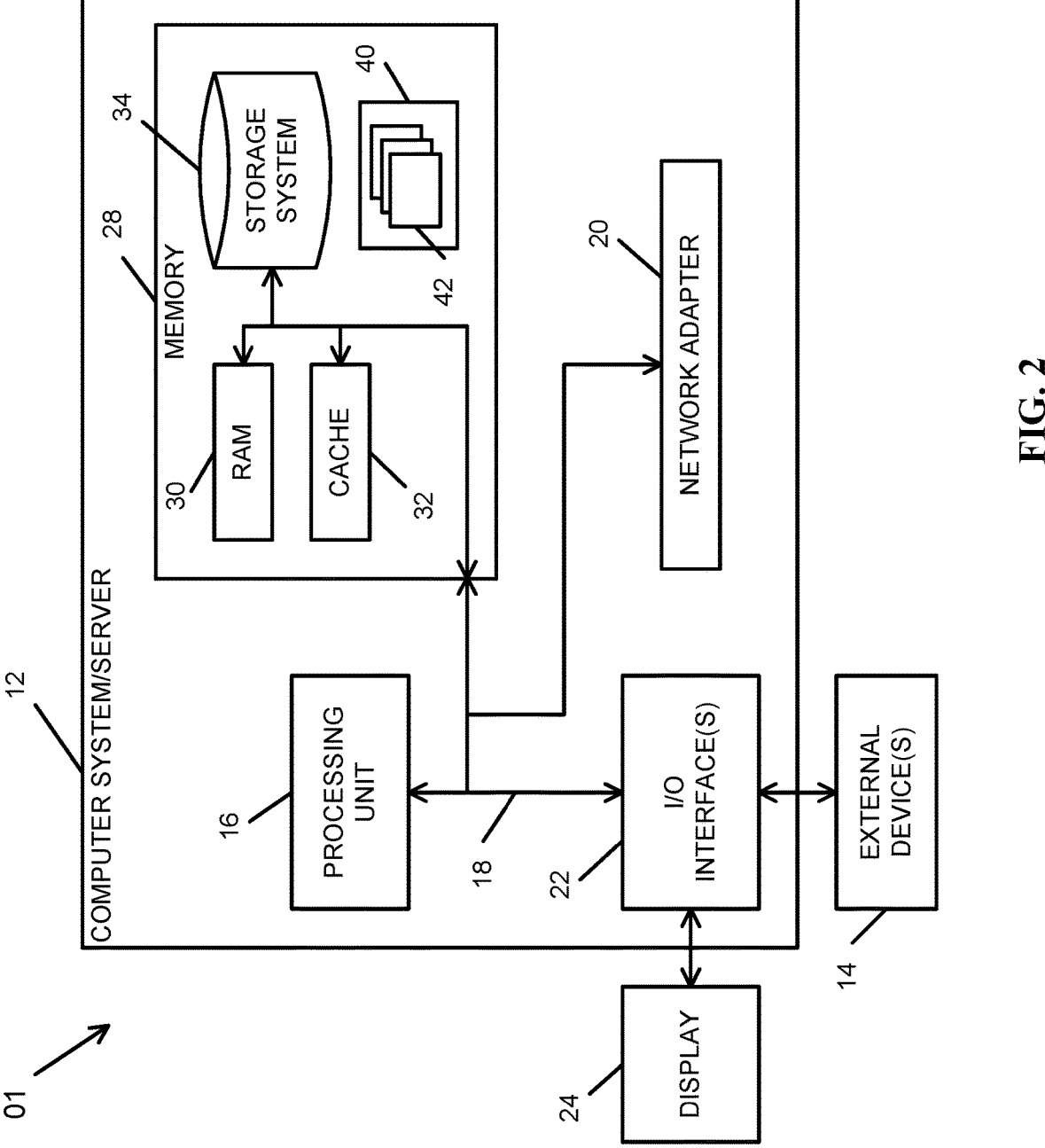
FIG. 2 depicts a computer system according to various embodiments of the present invention.

Aspects of the present disclosure relate to alleviating cherry-picking in radiology with artificial intelligence (AI). While the present disclosure is not necessarily limited to such applications, various aspects of the disclosure may be appreciated through a discussion of various examples using this context.

Image viewing software, such as picture archiving and communication systems (PACS), are used in healthcare organizations to securely store and digitally transmit electronic images and clinically-relevant reports. Radiologists use PACS to select and read exams. Exams to be read by each radiologist (where these exams to be read are compiled into worklists) can be chosen manually or assigned automatically (e.g., where an exam that assigned automatically is assigned autonomously and/or immediately upon creation by a computing system). A radiologist's productivity is measured in "difficulty" units for each exam type, typically RVUs (relative value units). However, RVUs do not always accurately denote the level of effort or time it takes a radiologist to read an exam. Thus, radiologists may cherry-pick the easiest exams to augment their workload and results, leaving the harder exams to sit in the queue. In some instances, "cherry-picking" refers to choosing exams to read with the goal of maximizing RVU output while minimizing effort, rather than reading exams in the order they appear (or in some other order that would be understood to be more fair, such as reading exams as prioritized by respective treating physicians).

Cherry-picking can become pervasive if not prevented, and prevention is difficult. Cherry-picking is becoming more common with larger, geographically dispersed groups such as teleradiology. Cherry-picking is still possible even with an automatic assignment system (i.e., rejecting assignments (can be for valid reasons but may also be for cherry-picking), reading out of order, etc.). As such, conventional medical systems may lack a technical ability to allocate or assign tasks in a way that adequately reduces the possibility of a radiologist cherry-picking said tasks to, e.g., bypass an intended apportionment of difficult tasks. In address these concerns, aspects of this disclosure provide an AI system that is configured to detect cherry-picking and modify the automatic exam assignments to prevent recurrence.

In some embodiments, to detect cherry-picking the AI system may examine sequences of read/rejected exams for each radiologist, detect types of exams that are preferentially selected or avoided, and categorize individual radiologists' behavior over some time period.

In some embodiments, to prevent cherry-picking the system may adjust a radiologist's worklist assignments. For example, the system may reduce weighting of preference criteria and increase weighting of fairness criteria for radiologists who exhibit cherry-picking behavior, apply rules to minimize out of order reading (for example, the system may set a maximum of 5 assigned studies for cherry-pickers, or not assign another study until the length of the worklist is less than 5), and generate a statistical report on findings and send to the quality assurance (QA) lead (e.g. system authority), allowing the team to handle the problem internally.

Normalizing Data

Normalizing data/normalization brings the entire probability distributions of adjusted values into alignment. A different approach to normalization of probability distributions is quantile normalization, where the quantiles of the different measures are brought into alignment.

In some embodiments, normalization refers to the creation of shifted and scaled versions of statistics, where the intention is that these normalized values allow the comparison of corresponding normalized values for different datasets in a way that eliminates the effects of certain gross influences, as in an anomaly time series. For example, data sets may include exam data, assigned radiologist data (e.g., name serial number, average RVU), the outcome of an exam (e.g. read, rejected, reassigned, etc.), and/or elapsed time data (turnaround time if the exam was read, time until the exam was rejected/reassigned, for manual assignment: time that passed before someone picked the exam). Some types of normalization involve only a rescaling, to arrive at values relative to some size variable, where such rescaling only making sense for ratio measurements (where ratios of measurements are meaningful), not interval measurements (where only distances are meaningful, but not ratios). In theoretical statistics, parametric normalization can often lead pivotal quantities (i.e., functions whose sampling distribution does not depend on the parameters) and to ancillary statistics (pivotal quantities that can be computed from observations, without knowing parameters). Normalization/normalizing data in statistics includes (a) standard score (normalizing errors when population parameters are known) (works well for populations that are normally distributed), (b) student's t-statistic (normalizing residuals when population parameters are unknown (estimated)), (c) studentized residual (normalizing residuals when parameters are estimated, particularly across different data points in regression analysis), (d) standardized moment (normalizing moments, using the standard deviation $\sigma$ as a measure of scale), (e) coefficient of variation (normalizing dispersion, using the mean $\mu$ as a measure of scale, particularly for positive distribution such as the exponential distribution and Poisson distribution), and (f) feature scaling used to bring all values into the range [0,1]. Features scaling may also be called unity-based normalization and can be generalized to restrict the range of values in the dataset between any arbitrary points.

Machine Learning

Machine learning (ML) relates to computer software/computer algorithms that can learn from and make predictions on data where such ML software surpasses the performance that could be achieved from following strictly static program instructions by making data-driven predictions or decisions that are output by, e.g., a trained ML model and/or algorithm (e.g., where this model/algorithm is trained from sample inputs). These machine learning models and algorithms can be said to "predict" what a "correct" output is based on a given set of inputs, such as via predictive analytics, where such analytical models allow researchers, data scientists, engineers, and analysts to produce reliable, repeatable decisions and results and uncover hidden insights through learning from historical relationships and trends in the data. In some embodiments, a machine learning computer software/computer algorithm/computer program utilizes exam data to determine a normal range of variables for particular classes of exams. In some embodiments, data for a first exam may be compared to the normal ranges to determine if an exam was rejected for reasons related to cherry-picking.

Machine Learning Tasks

Machine learning tasks are typically classified into three or four categories, depending on the nature of the learning signal or feedback available to a machine learning software/ algorithm/program. A first category is supervised learning, where the computer is presented with example inputs and their desired outputs, given by a teacher, with a goal of the computer learning a general rule that maps inputs to outputs. A second category of machine learning tasks includes unsupervised learning. For example, unsupervised learning could include receiving a list of cases that have been previously identified as being rejected due to cherry-picking where no labels are given to the machine learning algorithm and no human teacher guides the algorithm as it maps inputs to outputs. A third category is reinforcement learning where the machine learning computer program interacts with a dynamic environment in which it must perform a certain goal (such as detecting or reducing cherry-picking), where the machine learning program is provided feedback in terms of rewards and punishments as it navigates its problem space. A fourth category is semi-supervised learning, which is between supervised and unsupervised learning, where the teacher gives an incomplete training signal (i.e., a training set with some (often many) of the target outputs missing). Transduction is a special case of this principle where the entire set of problem instances is known at learning time, except that part of the targets are missing.

Machine learning tasks may also be categorized according to the desired output of the machine learning software/algorithm/program. For example, for machine learning with classification as the desired output, inputs are divided into two or more classes, and the learner/machine learning software must produce a model that assigns unseen inputs to one or more (multi-label classification) of these classes, where the inputs are exams and the classes are cherry-picked or not cherry-picked. As another example, for machine learning with regression as the desired output (a supervised problem), the outputs are continuous rather than discrete (e.g., likelihood of an exam having been cherry-picked from 0-100%). In addition, for machine learning with clustering as the desired output, a set of inputs is to be divided into groups, where the groups may not be known beforehand, making this typically an unsupervised task. Also, for machine learning with density estimation as the desired output, machine learning identifies the distribution of inputs in some space. As another example, for machine learning with dimensionality reduction as the desired output, machine learning simplifies inputs by mapping them into a lower-dimensional space, where topic modeling is a related problem, where a program is given a list of human language documents and is tasked to find out which documents cover similar topics.

Machine Learning Approaches

Machine learning software/algorithms/programs operate via different approaches. For example, decision tree learning uses a decision tree as a predictive model, which maps observations about an item to conclusions about the item's target value. Also, association rule learning is a method for discovering notable relations between variables in large databases. As another example, support vector machines (SVMs) are a set of related supervised learning methods used for classification and regression, where given a set of training examples, each marked as belonging to one of two categories, an SVM training algorithm builds a model that predicts whether a new example falls into one category or the other. Cluster analysis (unsupervised learning) is the assignment of a set of observations into subsets (called clusters) so that observations within the same cluster are similar according to some predesignated criterion or criteria, while observations drawn from different clusters are dissimilar, where different clustering techniques make different assumptions on the structure of the data, often defined by some similarity metric and evaluated for example by internal compactness (similarity between members of the same cluster) and separation between different clusters, with other methods being based on estimated density and graph connectivity.

Reinforcement learning is a machine learning approach which is concerned with how an agent ought to take actions in an environment so as to maximize some notion of reward, attempting to find a policy that maps states of the world to the actions the agent ought to take in those states, where neither correct input/output pairs are presented nor suboptimal actions are explicitly corrected. In similarity and metric learning, the machine learning software/algorithm/program is given pairs of examples that are considered similar and pairs of less similar objects and learns a similarity function (or a distance metric function) that can predict if new objects are similar.

Cognitive Computing

Cognitive computing describes technology platforms that are based on the scientific disciplines of artificial intelligence and signal processing. Cognitive computing platforms encompass machine learning, reasoning, natural language processing, speech recognition and vision (object recognition), human-computer interaction, dialog and narrative generation, and the like. A cognitive computing platform may be hardware and/or software that mimics the functioning of the human brain and helps to improve human decision-making. A cognitive computing system may learn at scale, reason with purpose, and interact with humans naturally. Cognitive computing systems may be adaptive, in that such systems may learn as information changes, and as goals and requirements evolve the systems may resolve ambiguity and tolerate unpredictability and may be engineered to feed on dynamic data in real time, or near real time. Cognitive computing systems may be interactive in that they may interact easily with users so that those users can define their needs comfortably, and they may also interact with other processors, devices, and cloud services, as well as with people. Also, cognitive computing systems may be iterative and stateful such that they may aid in defining a problem by asking questions or finding additional source input if a problem statement is ambiguous or incomplete, and they may remember previous interactions in a process and return information that is suitable for the specific application at that point in time. Cognitive computing systems may be contextual in that they may understand, identify, and extract contextual elements such as meaning, syntax, time, location, appropriate domain, regulations, user's profile, process, task and goal, and may draw on multiple sources of information, including both structured and unstructured digital information, as well as sensory inputs (visual, gestural, auditory, or sensor-provided).

Artificial Intelligence

Artificial intelligence is intelligence exhibited by machines, rather than humans or other animals. Artificial intelligence may be realized in any device that perceives its real or virtual environment and takes actions that maximize its chance of success at some goal, where such a machine mimics cognitive functions that humans associate with other human minds, such as learning and problem solving. Artificial intelligence may accomplish reasoning, knowledge, planning, learning, natural language processing (communication), perception and the ability to move and manipulate objects. Artificial intelligence may perform tasks by using statistical methods, computational intelligence, versions of search and mathematical optimization, logic, methods based on probability, and methods based on economics. An intelligent agent is a system/computer software/computer program/algorithm that perceives its real or virtual environment and takes actions which maximize its chances of success as described above, potentially using programs that solve specific problems (where these programs may use approaches such as symbolic and logical approaches and sub-symbolic neural networks). Agent architectures and cognitive architecture consist of interacting intelligent agents in a multi-agent system that includes both symbolic and sub-symbolic components that provides a bridge between sub-symbolic artificial intelligence and reactive levels and traditional symbolic intelligence, where relaxed time constraints permit planning and world modelling.

Regression Analysis

Regression analysis is a set of statistical processes for estimating the relationships among variables, possibly resulting in regression models. Regression analysis includes many techniques for modeling and analyzing several variables, when the focus is on the relationship between a dependent variable and one or more independent variables (i.e., predictors). More specifically, regression analysis helps one understand how the typical value of the dependent variable (i.e., criterion variable) changes when any one of the independent variables is varied, while the other independent variables are held fixed. Most commonly, regression analysis estimates the conditional expectation of the dependent variable given the independent variables (i.e., the average value of the dependent variable when the independent variables are fixed). Less commonly, the focus of regression analysis is on a quantile, or other location parameter of the conditional distribution of the dependent variable given the independent variables. In all cases, a function of the independent variables called the regression function is to be estimated.

In regression analysis, it is also of interest to characterize the variation of the dependent variable around the prediction of the regression function using a probability distribution. A related but distinct approach is necessary condition analysis (NCA), which estimates the maximum (rather than average) value of the dependent variable for a given value of the independent variable (ceiling line rather than central line) in order to identify what value of the independent variable is necessary but not sufficient for a given value of the dependent variable. Regression analysis is widely used for prediction and forecasting, where its use has substantial overlap with the field of machine learning. Regression analysis is also used to understand which among the independent variables are related to the dependent variable, and to explore the forms of these relationships. In restricted circumstances, regression analysis can be used to infer causal relationships between the independent and dependent variables.

Many techniques for carrying out regression analysis have been developed. Familiar methods such as linear regression and ordinary least squares regression are parametric, in that the regression function is defined in terms of a finite number of unknown parameters that are estimated from the data. Nonparametric regression refers to techniques that allow the regression function to lie in a specified set of functions, which may be infinite-dimensional. The performance of regression analysis methods in practice depends on the form of the data generating process, and how it relates to the regression approach being used. Since the true form of the data-generating process is generally not known, regression analysis often depends to some extent on making assumptions about this process, with such assumptions sometimes being testable if a sufficient quantity of data is available. Regression models for prediction are often useful even when the assumptions are moderately violated, although they may not perform optimally. In a narrower sense, regression may refer specifically to the estimation of continuous response (dependent) variables, as opposed to the discrete response variables used in classification. The case of a continuous dependent variable may be more specifically referred to as metric regression to distinguish it from related problems.

Current Technologies

Current system for tracking and assigning tasks to radiologists lack a technical ability to determine if a radiologist is cherry-picking cases. Current PACS systems lack a technical ability to identify abnormalities associated with reading or picking exams, and additionally lack a technical ability to analyze those abnormalities Problems with Current Technologies There is a need to be able to identify selection behavior that is indicative of cherry-picking with high accuracy, at least in order to be able to efficiently identify such behavior in a PACS system. Thus, there is a need to calculate aggregate forecasts of cherry-picking behavior for supervisors so that they can discourage such behavior to prevent backlogs of hard exams and thereby increase the burden on other radiologists.

FIG. 1 depicts an example method 100 of alleviating cherry-picking in radiology with artificial intelligence (AI). Operations of method 100 may be enacted by one or more computer systems such as the system described in FIG. 2 below.

Method 100 begins with operation 105 of receiving exam data. In some embodiments, exam data may contain relevant exam information (if available) such as: modality, specialty code, procedure code, priority, patient age, patient body mass index (BMI), symptoms, pain/no pain, post-op, recent cancer, location, outpatient, prior vs no prior exams, and normal vs abnormal lab work.

Method 100 continues with operation 110 of receiving radiologist data. In some embodiments, radiologist data may include radiologist status at the time of assignment: specialties, RVU assigned, radiologist dockets (worklist of exams) items, remaining capacity, etc.

Method 100 continues with operation 115 of training a neural network with a cherry-picking machine learning model based on the exam data and the radiologist data.

At operation 115, the neural network is trained to determine cherry-picking factors for exams. In some embodiments the nature of this training may vary based on, for example, the specialization of the component neural networks being trained, the input processed by those neural networks, or the output generated by those neural networks.

For example, a first neural network may be configured to ingest a corpus of data related to particular exams and output a probability that a particular candidate exam would be likely to be rejected by a radiologist that is cherry-picking. In an ontological structure, different data elements may form the "ground level" of the structure (e.g., the terminus from which no branches depend). Other data elements may be branches of the ontological structure. This first neural network would therefore be trained to understand what particular data elements make for the most effective organization of elements in order to lead to a determination that a particular case was cherry-picked. For example, reading time may be used by the first neural network as a baseline determination (ground level structure). If no exams that took under 2 minutes to read were rejected for cherry-picking, the system may configure the first neural network to remove all cases that took less than 15 minutes to read from being a cherry-picking candidate thereby decreasing the processing time of the neural network. Further, in some embodiments, the system may determine that those cases that are removed are useful to determine normal data elements that cherry-picking candidates should be evaluated in. For example, if many remove cases were selected within one hour of being put in a docket for a radiologist, cases that languished in the docket for over an hour may be an indicator for cherry-picking. In some embodiments, the first neural network may be trained on both manual worklist assignments (picked by radiologists) and automatic worklist assignments (automatically assigned by the system).

Clustering algorithms, such as those created with Isolation Forest methods, are pattern detection technique with many dimensions. Clustering enables an algorithm to learn from and detect patterns from raw data without explicit labels. This method suggests that normal data will cluster around one another, and anomalistic data are far from such clusters. In some embodiments, binary forests such as an Isolation Forest (IF) starts by utilizing all nodes to randomly select a dimension and afterwards randomly select a splitting threshold. The algorithm continues until each a single sample is allocated to each node. Via this method, an ensemble of trees may be created. Samples with unusual values (or outliers) have a higher chance to be isolated earlier on in the tree growing compared to samples in clusters, therefore the average depth/length of the sample within the trees in the ensemble leads directly to a cherry-picking score. Methods such as Elliptic Envelope (EV) can be used to fit data to a normal distribution and identify abnormalities. Afterwards the IF method may be used to find impacts within anomalistic data sets, however IF on its own is enough to detect anomalies which will include the impacts. While IF requires the number of trees to be determined by the user, it is needed in order to fully fetch out the anomalies within a data set which may hold the impacts thereby reducing the need for heavy filtering.

In an example, a first neural network may be trained, with an IF method, on a set of data from operations 105 and 110 consisting of (E, R, Y, T), where E is exam data, R is the assigned radiologist data, Y is the outcome (read, rejected, reassigned, etc.), and T is the time taken (turnaround time if the exam was read, time until the exam was rejected/reassigned, for manual assignment: time that passed before someone picked the exam). In this example, E contains relevant exam information (if available) such as: modality, specialty code, procedure code, priority, patient age, patient body mass index (BMI), symptoms, pain/no pain, post-op, recent cancer, location, outpatient, prior vs no prior, normal vs abnormal lab. In this example, R contains radiologist status at the time of assignment: specialties, RVU assigned, current worklist items, remaining capacity, etc.

Method 100 continues with operation 120 of configuring the first neural network to account for anomalous exams. In some embodiments, the system may determine that some factors may indicate an anomalous case that should not be evaluated for cherry-picking by the first neural network. In some instances, radiologists may specialize in certain areas. For example, a radiologist that specializes in chest x-rays may select those over mammograms. Likewise, in some instances, certain exams may require special training that not all radiologists possess. For example, if only 1% of radiologists read head computed tomographs (CTs) then those may be taken out of consideration for cherry-picking evaluation.

Method 100 continues with operation 125 of receiving a radiologist's reading history. In some embodiments, the radiologist's reading history includes the radiologist's docket decisions and data for one or more exams that were read. For example, docket decisions may include the exams that were read and/or selected and data for the one or more exams may include data for the exams that were read and/or selected. In some embodiments, the radiologist's reading history may be augmented by running the exams in the radiologist's reading history through the first neural network, from operation 115 and 120, and including the results in the radiologist's reading history.

In some embodiments, an autoencoder type of artificial neural network may be used to learn efficient codings of unlabeled data. The encoding is validated and refined by attempting to regenerate the input from the encoding. The autoencoder learns a representation (encoding) for a set of data, here radiologist's reading history, typically for dimensionality reduction, by training the network to ignore insignificant data ("noise").

The neural network may learn representations to assume useful properties. In some embodiments, the neural network may be used as a generative model to randomly generate new data that is similar to the input data (training data).

In some embodiments, the auto encoder may have two parts: an encoder that maps the input into the code, and a decoder that maps the code to a reconstruction of the input. The autoencoder may be directed to reconstruct the input approximately, preserving only the most relevant aspects of the data in the copy. The reconstruction may be used as a norm for a radiologist's reading history.

In some embodiments, the autoencoder may be a feed-forward, non-recurrent neural network similar to single layer perceptrons that participate in multilayer perceptrons (MLP)—employing an input layer and an output layer connected by one or more hidden layers. In some embodiments, the output layer has the same number of nodes (neurons) as the input layer. In some embodiments, a purpose of the non-recurrent neural network may be to reconstruct its inputs (minimizing the difference between the input and the output) instead of predicting a target value for the given inputs creating an unsupervised neural network. An autoencoder may be used in a similar manner to create the first neural network in operation 115.

Method 100 continues with operation 130 of generating a scoring decision for a radiologist using the first isolation tree and the second neural network. In some embodiments, the decision may be a percent likelihood that the radiologist is cherry-picking, with a list of exams that the radiologist rejected that are indicated to be the result of cherry-picking. For example, the system may use the second neural network to give the radiologist a score, e.g., 75% likely to be cherry-picking, and the system may use the second neural network to identify a list of exams that the radiologist rejected that are likely to be cherry-picked with a score for each exam, e.g., exam 1 80% likely to have been rejected due to cherry-picking, etc. In some embodiments, an autoencoder may be trained to produce a compact representation of a radiologist's reading history during some time period. The autoencoder may be trained using only radiologist data containing exams with low cherry-picking scores as determined by the isolation forest. These radiologists are unlikely to be cherry-pickers; therefore, the autoencoder learns a compact representation that only applies to non-cherry-picking radiologists. To classify a new radiologist as cherry-picking or not, their reading history may be encoded and decoded using the autoencoder. If the radiologist is not a cherry-picker, the encoding should be highly accurate, so a value very similar to the original input should be obtained after encoding and decoding the data with the autoencoder. Conversely, in some embodiments, if the radiologist is a cherry-picker, the autoencoder has not learned an accurate representation of their data. So, the encoding and decoding (reconstruction) process using the autoencoder should leave the data significantly different from the original input. By applying a threshold to the difference between the original input and the reconstructed data, the system may then identify cherry-picking radiologists as those who show high reconstruction error.

In some embodiments, operation 135 may include adjusting automatic exam assignments to a cherry-picking radiologist by reducing a weighting of preference criteria and increasing the weighting of fairness criteria. In some instances, the preference criteria may be an availability of exams likely to be picked for cherry-picking reasons. In some embodiments, the fairness criteria may preferentially give a radiologist who is performing cherry-picking more difficult exams to counteract the cherry-picking. In some embodiments, the system may apply rules to minimize cherry-picking and prevent out-of-order reading. For example, the system may assign a set of five exams to the radiologist, and prevent them from receiving another set of five exams until those five are completed. As another example, the system may prevent the radiologist from selecting exams that are more recent than unread exams currently in their worklist, with a tolerance that can be configured by the site administrator (e.g., system authority).

In an exemplary embodiment, the system includes computer system 01 as shown in FIG. 2 and computer system 01 may perform one or more of the functions/processes described above. Computer system 01 is only one example of a computer system and is not intended to suggest any limitation as to the scope of use or functionality of embodiments of the present invention. Regardless, computer system 01 is capable of being implemented to perform and/or performing any of the functionality/operations of the present invention.

Computer system 01 includes a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices.

Computer system/server 12 may be described in the general context of computer system-executable instructions, such as program modules, being executed by a computer system. Generally, program modules may include routines, programs, objects, components, logic, and/or data structures that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 2, computer system/server 12 in computer system 01 is shown in the form of a general-purpose computing device. The components of computer system/ server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system/server 12 typically includes a variety of computer system readable media. Such media may be any available media that is accessible by computer system/server 12, and includes both volatile and non-volatile media, removable and non-removable media.

System memory 28 can include computer system readable media in the form of volatile memory, such as random access memory (RAM) 30 and/or cache memory 32. Computer system/server 12 may further include other removable/ non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As is further depicted and described below, memory 28 may include at least one program product having a set (e.g., at least one) of program modules that are configured to carry out the functions/operations of embodiments of the invention.

Program/utility 40, having a set (at least one) of program modules 42, may be stored in memory 28 by way of example, and not limitation. Exemplary program modules 42 may include an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the present invention.

Computer system/server 12 may also communicate with one or more external devices 14 such as a keyboard, a pointing device, a display 24, one or more devices that enable a user to interact with computer system/server 12, and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN)

or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

Cloud Computing

It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Figure 3:
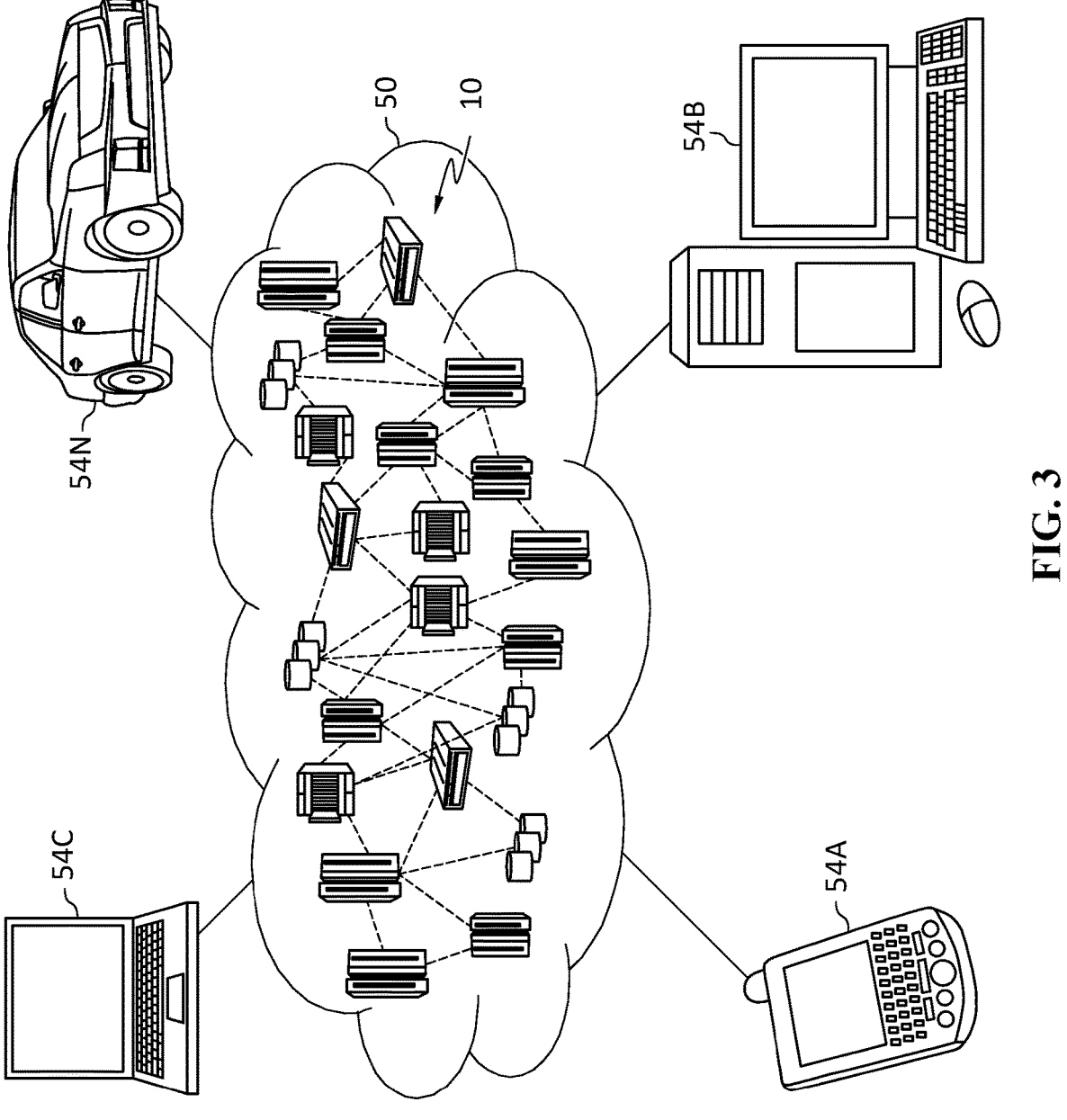
FIG. 3 depicts a cloud computing environment according to various embodiments of the present invention.

Referring now to FIG. 3, illustrative cloud computing environment 50 is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 3 are intended to be illustrative only and that computing nodes 10 and cloud computing environment 50 can communicate with any type of computerized device over any type of network and/or network addressable connection (e.g., using a web browser).

Figure 4:
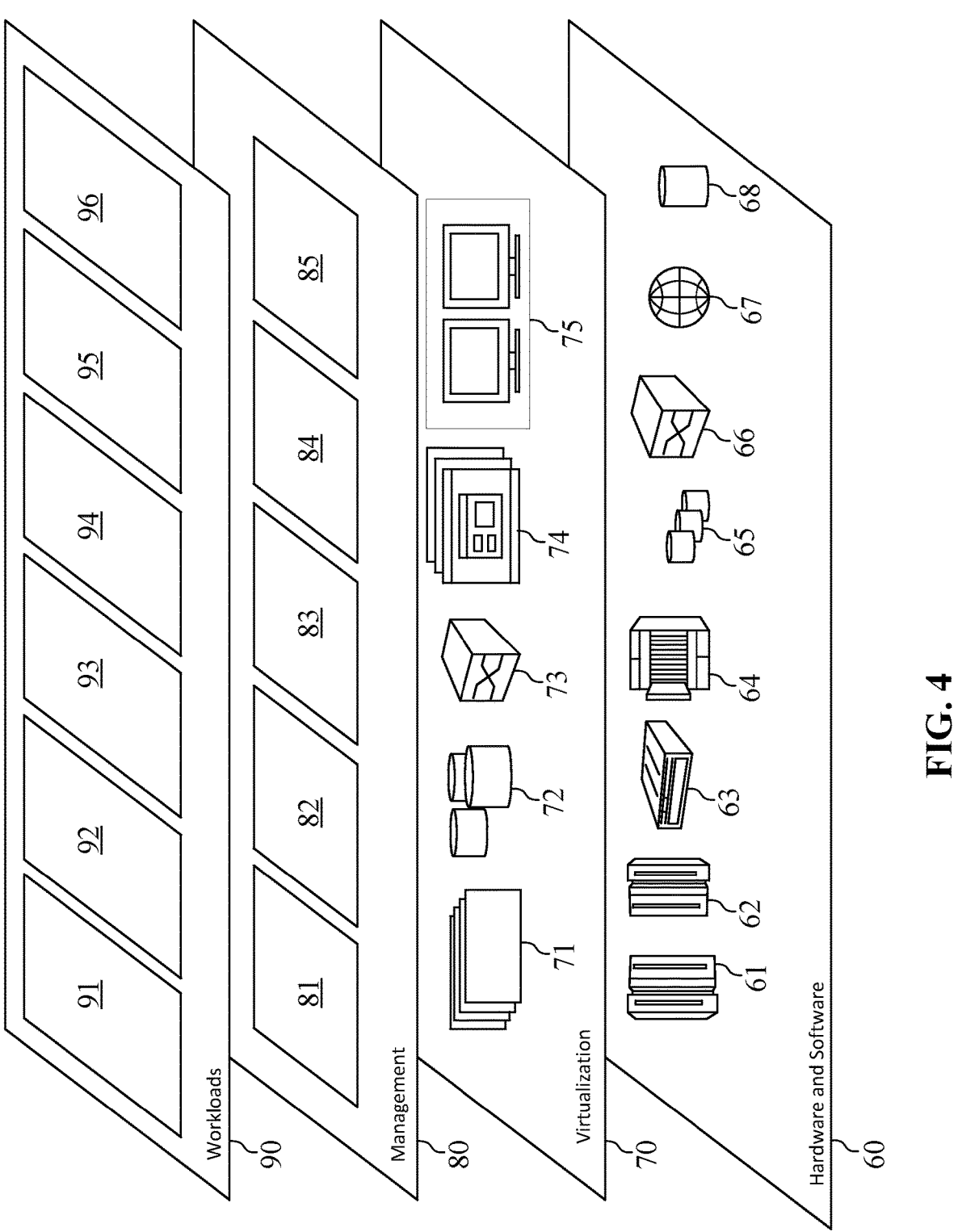
FIG. 4 depicts abstraction model layers according to various embodiments of the present invention.

Referring now to FIG. 4, a set of functional abstraction layers provided by cloud computing environment 50 (FIG. 3) is shown. It should be understood in advance that the components, layers, and functions shown in FIG. 4 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and predictive neural networks 96.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present disclosure have been presented for purposes of illustration but are not intended to be exhaustive or limited to the embodiments disclosed. Many modifications and variations will be apparent to those of ordinary skill in the art without departing from the scope and spirit of the described embodiments. The terminology used herein was chosen to explain the principles of the embodiments, the practical application or technical improvement over technologies found in the marketplace, or to enable others of ordinary skill in the art to understand the embodiments disclosed herein.

What is claimed is:

1. A system comprising:
a memory; and
a processor in communication with the memory, the processor being configured to:
  receive radiology data, outcome data, and elapsed time data for one or more exams;
  train a first machine learning model using the radiology data, the outcome data, and the elapsed time data to detect exams that are candidates for cherry-picking and to account for anomalous exams that should not be evaluated for cherry-picking;
  receive a radiologist reading history;
  augment the radiologist reading history with a likelihood that an exam in the radiologist reading history was rejected due to cherry-picking by running the radiologist reading history through the first machine learning model;
  generate a cherry-picking score for a radiologist by application of a second machine learning model on the radiologist reading history; and adjust automatic exam assignments based on a determination that the cherry-picking score exceeds a threshold, by increasing a weighting of fairness criteria and reducing a weighting of preference criteria.

2. The system of claim 1, wherein the processor is further configured to:

train the second machine learning model to detect cherry-picking behavior by radiologists using the augmented radiology data, the outcome data, and the elapsed time data.

3. The system of claim 2, wherein the processor is further configured to issue a restriction on a radiologist from selecting exams that are more recent than unread exams currently in a worklist for the radiologist, based on a determination that the cherry-picking score exceeds a threshold.

4. The system of claim 1, wherein the processor is further configured to apply rules to minimize cherry-picking and prevent out-of-order reading.

5. The system of claim 1, wherein the processor is further configured to generate a statistical report to be sent to a system authority.

6. The system of claim 1, wherein the radiology data is selected from the group consisting of a medical exam, data regarding individual radiologists, an outcome of the one or more exams, and the elapsed time data for the one or more exams.

7. A computer-implemented method, comprising:

receiving radiology data, outcome data, and elapsed time data for one or more exams;

training a first machine learning model using the radiology data, the outcome data, and the elapsed time data to detect exams that are candidates for cherry-picking and to account for anomalous exams that should not be evaluated for cherry-picking;

receiving a radiologist reading history;

augmenting the radiologist reading history with a likelihood that an exam in the radiologist reading history was rejected due to cherry-picking by running the radiologist reading history through the first machine learning model;

generating a cherry-picking score for a radiologist by application of a second machine learning model on the radiologist reading history; and adjusting automatic exam assignments based on a determination that the cherry-picking score exceeds a threshold, by increasing a weighting of fairness criteria and reducing a weighting of preference criteria.

8. The computer-implemented method of claim 7, further comprising:

training the second machine learning model to detect cherry-picking behavior by radiologists using the augmented radiology data, the outcome data, and the elapsed time data.

9. The computer-implemented method of claim 8, further comprising issuing a restriction on a radiologist to prevent the radiologist from selecting exams that are more recent than unread exams currently in a worklist for the radiologist, based on a determination that the cherry-picking score exceeds a threshold.

10. The computer-implemented method of claim 7, further comprising applying rules to minimize cherry-picking and prevent out-of-order reading.

11. The computer-implemented method of claim 7, further comprising generating a statistical report to be sent to a system authority.

12. The computer-implemented method of claim 7, wherein the radiology data is selected from the group consisting of a medical exam, data regarding individual radiologists, an outcome of the one or more exams, and the elapsed time data for the one or more exams.

13. A computer program product comprising a computer readable storage medium having program instructions embodied therewith, the program instructions executable by a processor to cause the processor to perform a method, the method comprising:

receiving radiology data, outcome data, and elapsed time data for one or more exams;

training a first machine learning model using the radiology data, the outcome data, and the elapsed time data to detect exams that are candidates for cherry-picking and to account for anomalous exams that should not be evaluated for cherry-picking;

receiving a radiologist reading history;

augmenting the radiologist reading history with a likelihood that an exam in the radiologist reading history was rejected due to cherry-picking by running the radiologist reading history through the first machine learning model;

generating a cherry-picking score for a radiologist by application of a second machine learning model on the radiologist reading history; and adjusting automatic exam assignments based on a determination that the cherry-picking score exceeds a threshold, by increasing a weighting of fairness criteria and reducing a weighting of preference criteria.

14. The computer program product of claim 13, wherein the method further comprises:

training the second machine learning model to detect cherry-picking behavior by radiologists using the augmented radiology data, the outcome data, and the elapsed time data.

15. The computer program product of claim 14, wherein the method further comprises issuing a restriction on a radiologist to prevent the radiologist from selecting exams that are more recent than unread exams currently in a worklist of the radiologist, based on a determination that the cherry-picking score exceeds a threshold.

16. The computer program product of claim 13, wherein training the first machine learning model is based on:

specialization of component neural networks being trained, radiology data processed by the neural networks, and the output generated by the neural networks.

17. The computer program product of claim 13, wherein the method further comprises:

generating a clustering algorithm for pattern detection technique with multiple dimensions, wherein clustering enables an algorithm to learn from and detect patterns from raw data without explicit labels;

utilizing all nodes to randomly select a dimension and afterwards randomly select a splitting threshold;

creating an ensemble of trees, wherein samples with unusual values have a higher chance to be isolated earlier on in a tree growing compared to samples in clusters; and determining, based on an average depth of a sample within the trees, a cherry-picking score, wherein an Isolation Forest (IF) method is used to find impacts within anomalistic data sets.

* * * * *